United States Patent
Ushiro et al.

(10) Patent No.: US 11,000,636 B2
(45) Date of Patent: May 11, 2021

(54) COPOLYMER AND MEDICAL MATERIAL CONTAINING THE SAME

(71) Applicant: Toray Industries, Inc., Tokyo (JP)

(72) Inventors: Suguru Ushiro, Otsu (JP); Akihiro Hayashi, Otsu (JP); Yoshiyuki Ueno, Otsu (JP)

(73) Assignee: Toray Industries, Inc., Tokyo (JP)

( * ) Notice: Subject to any disclaimer, the term of this patent is extended or adjusted under 35 U.S.C. 154(b) by 166 days.

(21) Appl. No.: 16/333,615

(22) PCT Filed: Sep. 20, 2017

(86) PCT No.: PCT/JP2017/033848
§ 371 (c)(1),
(2) Date: Mar. 15, 2019

(87) PCT Pub. No.: WO2018/061916
PCT Pub. Date: Apr. 5, 2018

(65) Prior Publication Data
US 2019/0255227 A1    Aug. 22, 2019

(30) Foreign Application Priority Data
Sep. 30, 2016  (JP) .............................. JP2016-193597

(51) Int. Cl.
| | | |
|---|---|---|
| *A61L 33/06* | (2006.01) | |
| *A61L 33/00* | (2006.01) | |
| *C08L 31/02* | (2006.01) | |
| *C08L 33/26* | (2006.01) | |
| *C08L 39/02* | (2006.01) | |
| *C08L 39/04* | (2006.01) | |
| *C08F 226/00* | (2006.01) | |

(52) U.S. Cl.
CPC ......... *A61L 33/064* (2013.01); *A61L 33/0088* (2013.01); *A61L 33/06* (2013.01); *C08F 226/00* (2013.01); *C08L 31/02* (2013.01); *C08L 33/26* (2013.01); *C08L 39/02* (2013.01); *C08L 39/04* (2013.01); *C08L 2203/02* (2013.01)

(58) Field of Classification Search
None
See application file for complete search history.

(56) References Cited

U.S. PATENT DOCUMENTS

| | | | | |
|---|---|---|---|---|
| 2014/0142613 | A1* | 5/2014 | Inoue ................. | A61L 33/0041 606/200 |
| 2014/0296441 | A1* | 10/2014 | Hood .................... | C08F 226/10 525/303 |
| 2014/0342954 | A1* | 11/2014 | Ingber .................... | A61L 29/14 508/100 |

FOREIGN PATENT DOCUMENTS

| | | |
|---|---|---|
| EP | 2 724 732 A1 | 4/2014 |
| JP | 58-156082 A | 9/1983 |
| JP | 3497612 B2 | 2/2004 |
| JP | 2007-226018 A | 9/2007 |
| JP | 4152075 B2 | 7/2008 |
| JP | 4273965 B2 | 3/2009 |
| JP | 4888559 B2 | 12/2011 |
| JP | 2013-222141 | 10/2013 |
| JP | 5857407 B2 | 12/2015 |
| WO | 2012/176861 A1 | 12/2012 |
| WO | 2015/080176 A1 | 6/2015 |
| WO | 2016/158388 A1 | 10/2016 |

OTHER PUBLICATIONS

The Extended European Search Report dated Apr. 23, 2020, of counterpart European Application No. 17855711.4.
Office Action dated Jul. 29, 2020, of counterpart Indian Application No. 201947013667.

* cited by examiner

*Primary Examiner* — Robert T Butcher
(74) *Attorney, Agent, or Firm* — DLA Piper LLP (US)

(57) ABSTRACT

A copolymer is capable of being immobilized on a base material while maintaining a high antithrombotic property persistently without having to introduce heparin or an anticoagulant drug to the surface thereof. The copolymer includes monomer unit A, monomer unit B, and monomer unit C, wherein monomer unit C has a mole fraction of 0.5-40% with respect to the total amount of all constituent monomer units.

12 Claims, 2 Drawing Sheets

COPOLYMER AND MEDICAL MATERIAL CONTAINING THE SAME

TECHNICAL FIELD

This disclosure relates to a copolymer and a medical material containing the same.

BACKGROUND

Medical materials and medical devices that come into contact with blood (for example, artificial kidneys, artificial lungs, artificial blood vessels, artificial valves, stents, stent grafts, catheters, thrombus capture devices, angioscopes, suture threads, blood circuits, tubes, cannulas, blood bags, and syringes) are required to have potent antithrombotic properties to prevent hypofunction due to coagulation of blood. Heretofore, to improve the antithrombotic properties of medical materials and medical devices, there has been employed a technique of imparting heparin or a heparin derivative as an anticoagulant drug to a surface of a base material.

An example of a reported method of imparting heparin or a heparin derivative to a surface of a base material is a method of immobilizing heparin or a heparin derivative by ionic bond with a positively charged cationic compound introduced onto a surface of a base material (Japanese Patent Nos. 4152075, 3497612 and 4273965).

Meanwhile, as a method of bonding an antithrombotic compound other than heparin or a heparin derivative to a surface of a base material, there has been reported a method of immobilizing a compound having antithrombin activation performance onto a surface of a base material (International Publication Nos. 2012/176861 and 2015/080176).

Moreover, there has also been reported a method of crosslinking and immobilizing a vinylpyrrolidone/vinyl acetate copolymer having platelet adhesion suppressing performance onto a surface of a base material made of a hollow fiber membrane by radiation irradiation in water (Japanese Patent Nos. 4888559 and 5857407).

The technique of imparting heparin or a heparin derivative to a surface of a base material as in JP '075, JP '612 and JP '965, however, cannot be used in patients with heparin-induced thrombocytopenia or patients with bleeding. Moreover, since heparin and heparin derivatives are animal-derived components, attention must be paid to administration and handling of such compounds.

In addition, the technique of imparting a compound having antithrombin activation performance to a surface of a base material described in WO '861 and WO '176 is difficult to use in patients with bleeding because it may be difficult to stop bleeding during the treatment if the compound elutes. Moreover, the compound having antithrombin activation performance is much more expensive than polymer compounds and the like because it is an anticoagulant drug.

The vinylpyrrolidone/vinyl acetate copolymer described in JP '559 and JP '407, when being used in a medical device that may be used for over a day in the body such as a stent or a catheter may cause thrombosis on a surface of a base material due to long-time use. In addition, the copolymer can be immobilized onto the surface of the base material only by crosslinking and immobilization through radiation irradiation. Therefore, the copolymer may not sufficiently exhibit antithrombotic properties due to three-dimensional crosslinking or modification thereof.

It could therefore be helpful to provide a copolymer that can be immobilized onto a base material while maintaining potent antithrombotic properties persistently without the need for introduction of heparin or an anticoagulant drug onto a surface of a base material, and a medical material containing the copolymer.

SUMMARY

We thus provide:

(1) A copolymer comprising a monomer unit A, a monomer unit B, and a monomer unit C that are represented by general formula (I), wherein the mole fraction of the monomer unit C based on all the monomer units that constitute the copolymer is 0.5 to 40%:

A

(I)

B

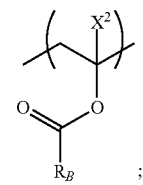

C

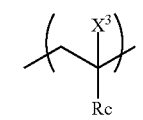

wherein $R_A$ represents a functional group having an amide bond, $R_B$ represents an alkyl or an alkenyl having 2 to 20 carbon atoms, $R_C$ represents an alkyl or an alkenyl in which an arbitrary hydrogen atom is substituted with at least one functional group selected from the group consisting of an amino group, an azido group, an imino group, a carboxy group, an acid chloride group, an acid anhydride group, an aldehyde group, a hydroxyl group, a phosphoric acid group, a thiol group, an isocyanate group, a thioisocyanate group, an epoxy group, a halogenated alkyl group, a cyano group, a vinyl group, an ethynyl group, a nitro group and a nitroso group, and ionized functional groups thereof (wherein an arbitrary carbon atom in the alkyl or the alkenyl of $R_C$ is optionally substituted with a nitrogen atom, an oxygen atom, or a sulfur atom), and $X^1$, $X^2$, and $X^3$ each represent a hydrogen atom or a methyl group.

(2) The copolymer according to (1), wherein the monomer unit A is represented by any one of general formulae (II) to (IV):

A-1

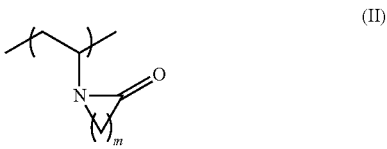

(II)

A-2

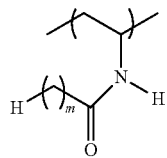

(III)

A-3

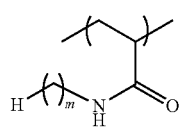

(IV)

wherein m represents an integer of 1 to 5.

(3) The copolymer according to (1) or (2), wherein the monomer unit A, the monomer unit B, and the monomer unit C are randomly arranged.

(4) The copolymer according to any one of (1) to (3), having a number average molecular weight of 1,000 to 100,000.

(5) The copolymer according to any one of (1) to (4), wherein $R_C$ is an alkyl group in which an arbitrary hydrogen atom is substituted with at least one functional group selected from an amino group, an isocyanate group, and an epoxy group.

(6) A medical material containing the copolymer according to any one of (1) to (5), and a base material bonded to the copolymer.

(7) The medical material according to (6), wherein the base material is made from a polymer having a repeating unit containing an ester bond in a main chain.

(8) The medical material according to (6), further containing a phosphonic acid derivative or a catechol derivative, wherein the base material is made of a metal, the copolymer is bonded to the phosphonic acid derivative or the catechol derivative, the phosphonic acid derivative is bonded to the base material via a phosphonic acid group thereof, and the catechol derivative is bonded to the base material via a catechol group thereof.

(9) A thrombus capture device including the medical material according to any one of (6) to (8).

(10) The medical material according to (6), wherein the base material is made from a polymer a part of which contains a hydroxyl group or a carboxy group introduced therein and in which at least one hydrogen atom in a main chain is substituted with a chlorine atom, or a polymer a part of which contains a hydroxyl group or a carboxy group introduced therein and that has a siloxane bond in at least a part thereof, and the copolymer is bonded to the base material via the hydroxyl group or the carboxy group.

(11) A blood circuit including the medical material according to (10).

(12) A copolymer comprising a monomer unit A, a monomer unit B, and a monomer unit C that are represented by general formula (I), wherein the mole fraction of the monomer unit C based on all the monomer units that constitute the copolymer is 0.5 to 40%:

A

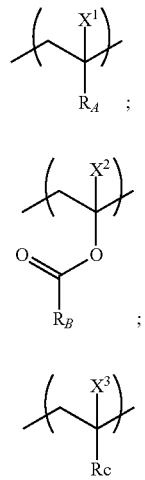

wherein $R_A$ represents a functional group having an amide bond, $R_B$ represents an alkyl or an alkenyl having 2 to 20 carbon atoms, and $R_C$ represents an alkyl or an alkenyl in which an arbitrary hydrogen atom is substituted with at least one functional group selected from the group consisting of an amino group, an azido group, an imino group, a carboxy group, an acid chloride group, an acid anhydride group, an aldehyde group, a hydroxyl group, a phosphoric acid group, a thiol group, an isocyanate group, a thioisocyanate group, an epoxy group, a halogenated alkyl group, a cyano group, a vinyl group, an ethynyl group, a nitro group or a nitroso group, or ionized functional groups thereof (wherein an arbitrary carbon atom in the alkyl or the alkenyl of $R_C$ is optionally substituted with a nitrogen atom, an oxygen atom, or a sulfur atom).

(13) The copolymer according to (12), wherein the monomer unit A is represented by general formulae (II) to (IV):

A-1

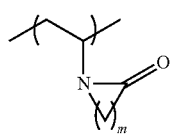

(II)

A-2

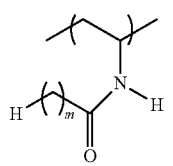

(III)

A-3

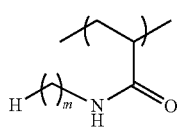

(IV)

wherein m represents an integer of 1 to 5.

(14) The copolymer according to (12) or (13), wherein the monomer unit A, the monomer unit B, and the monomer unit C are randomly arranged.

(15) The copolymer according to any one of (12) to (14), having a number average molecular weight of 1,000 to 100,000.

(16) The copolymer according to any one of (12) to (15), wherein $R_C$ is an amino group.

(17) A medical material containing the copolymer according to any one of (1) to (5), and a base material bonded to the copolymer.

(18) The medical material according to (17), wherein the base material is made from a polyester-based polymer.

(19) A medical material containing the copolymer according to any one of (12) to (16), a phosphonic acid derivative or a catechol derivative, and a base material made of a metal, wherein the copolymer is bonded to the phosphonic acid derivative or the catechol derivative, the phosphonic acid derivative is bonded to the base material via a phosphonic acid group thereof, and the catechol derivative is bonded to the base material via a catechol group thereof.

(20) A thrombus capture device including the medical material according to any one of (17) to (19).

Since the copolymer can be immobilized onto a base material while maintaining potent antithrombotic properties persistently, the copolymer can be preferably used in a medical material and a thrombus capture device that require antithrombotic properties.

DESCRIPTION OF REFERENCE SIGNS

Figure 1:
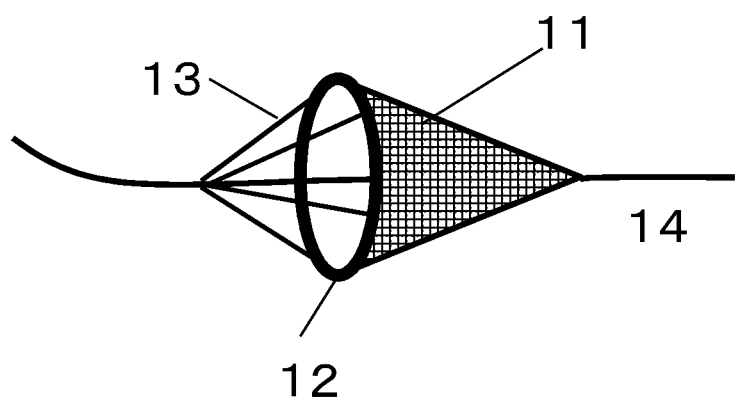
FIG. 1 shows a thrombus capture device according to a first example, the device including our copolymer.

11: Filter
12: Ring-shaped part
13: Support line part
14: Core part
21: Filter
22: Cylindrical support part
23: Core part
31: Thrombus capture device
32: Blood circuit
33: Pump
34: Blood
35: Centrifuge tube

DETAILED DESCRIPTION

Our copolymer comprises a monomer unit A, a monomer unit B, and a monomer unit C that are represented by general formula (I), and the mole fraction of the monomer unit C based on all the monomer units that constitute the copolymer is 0.5 to 40%:

A

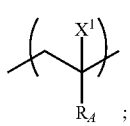

(I)

B

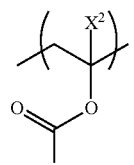

C

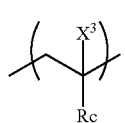

wherein $R_A$ represents a functional group having an amide bond, $R_B$ represents an alkyl or an alkenyl having 2 to 20 carbon atoms, $R_C$ represents an alkyl or an alkenyl in which an arbitrary hydrogen atom is substituted with at least one functional group selected from the group consisting of an amino group, an azido group, an imino group, a carboxy group, an acid chloride group, an acid anhydride group, an aldehyde group, a hydroxyl group, a phosphoric acid group, a thiol group, an isocyanate group, a thioisocyanate group, an epoxy group, a halogenated alkyl group, a cyano group, a vinyl group, an ethynyl group, a nitro group and a nitroso group, and ionized functional groups thereof (wherein an arbitrary carbon atom in the alkyl or the alkenyl of $R_C$ is optionally substituted with a nitrogen atom, an oxygen atom, or a sulfur atom), and $X^1$, $X^2$, and $X^3$ each represent a hydrogen atom or a methyl group.

Unless otherwise specified, the terms used herein are defined as follows.

A "copolymer" refers to a polymer compound obtained by copolymerizing two or more kinds of monomers.

A "monomer unit" refers to a repeating unit in a homopolymer or copolymer obtained by polymerizing monomers.

The copolymer may comprise one kind or two or more kinds of the monomer unit A, the monomer unit B, and the monomer unit C each.

It is preferable to use, as the monomer unit A, a hydrophilic monomer having an amide bond such as N-vinylacetamide, N-vinylpropylamide, N-methylvinylacetamide, vinylpyrrolidone, vinylcaprolactam, acrylamide, N-methylacrylamide, N,N-dimethylacrylamide or amidoalkyl (meth)acrylate since these monomers do not have too strong hydrophilicity. This is because too high hydrophilicity may cause destabilization of the structure of platelets or proteins and may cause thrombosis, although it is effective to hydrophilize the base material of the medical material to suppress the adhesion of platelets or proteins.

A "hydrophilic monomer" is defined as a monomer a homopolymer of which (having a number average molecular weight of 1,000 or more and 50,000 or less) is easily soluble in water. "Easily soluble in water" means that the relevant substance has a solubility exceeding 1 g, preferably 10 g or more in 100 g of pure water at 20° C.

Above all, the monomer unit A is preferably represented by any one of general formulae (II) to (IV) since such a monomer unit enables synthesis of the copolymer by radical polymerization and has neither too strong hydrophilicity nor too strong hydrophobicity:

A-1

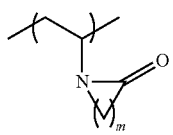

(II)

A-2

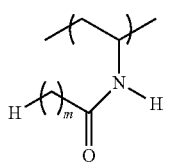

(III)

A-3

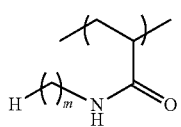

(IV)

wherein m represents an integer of 1 to 5.

m is preferably an integer of 1 to 5 so that the monomer unit A may not have too strong hydrophilicity or hydrophobicity.

Examples of the monomer unit of general formula (II) include vinylpyrrolidone (m=3) and vinylcaprolactam (m=5).

Examples of the monomer unit of general formula (III) include N-vinylacetamide (m=1) and N-vinylpropylamide (m=2).

Examples of the monomer unit of general formula (IV) include N-methylacrylamide (m=1) and N-butylacrylamide (m=4).

In particular, the monomer unit A is preferably a monomer unit represented by general formula (II) or (III) because of ease of copolymerization with the monomer unit B, and is more preferably vinylpyrrolidone or N-vinylacetamide because of high safety to the human body.

The monomer unit B has, as $R_B$, an alkyl or an alkenyl having 2 to 20 carbon atoms. When the number of carbon atoms is small, the copolymer as a whole has low mobility and does not exhibit adhesion suppressing performance for platelets and proteins. On the other hand, when the number of carbon atoms is large, the copolymer as a whole has strong hydrophobicity, and induces adhesion of platelets or proteins. The number of carbon atoms of $R_B$ is more preferably 2 to 9, still more preferably 2 to 5.

$R_B$ may represent a linear, branched, or cyclic alkyl or a linear, branched, or cyclic alkenyl bonded to a carbon atom of an ester group present in a side chain of the monomer unit B. For example, in vinyl acetate, $R_B$ represents $CH_3$—, and in the case of vinyl butyrate, $R_B$ represents $CH_3CH_2CH_2$—. $R_B$ is not limited to a linear group such as an ethyl group, an n-propyl group, an n-butyl group, an n-pentyl group, and an n-hexyl group, and may be a branched group such as an isopropyl group and a tertiary butyl group, or a cyclic group such as a cyclopropyl group, a cyclobutyl group, and a phenyl group. From the viewpoint of availability, a linear group is preferable. In addition, $R_B$ may be either aliphatic or aromatic, but is preferably aliphatic from the viewpoint of antithrombotic properties. Furthermore, $R_B$ may have a heteroatom such as a nitrogen atom or an oxygen atom, but is preferably formed only of a carbon atom and a hydrogen atom from the viewpoint of availability.

The "number of carbon atoms" refers to the number of carbon atoms that constitute $R_B$. For example, vinyl acetate has a number of carbon atoms of 1, and vinyl butyrate has a number of carbon atoms of 3.

Furthermore, the copolymer comprises the monomer unit C. In the monomer unit C, $R_C$ represents an alkyl or an alkenyl in which an arbitrary hydrogen atom is substituted with at least one functional group selected from the group consisting of an amino group, an azido group, an imino group, a carboxy group, an acid chloride group, an acid anhydride group, an aldehyde group, a hydroxyl group, a phosphoric acid group, a thiol group, an isocyanate group, a thioisocyanate group, an epoxy group, a halogenated alkyl group, a cyano group, a vinyl group, an ethynyl group, a nitro group and a nitroso group, and ionized functional groups thereof. An arbitrary carbon atom in the alkyl or alkenyl of $R_C$ is optionally substituted with a nitrogen atom, an oxygen atom, or a sulfur atom. The alkyl or alkenyl of $R_C$ may be linear, branched, or cyclic, and may have an aromatic ring.

Above all, the functional group of $R_C$ in the monomer unit C is preferably an amino group, a carboxy group, or an epoxy group from the viewpoint of stability during the synthesis of the copolymer. In addition, a hydroxyl group and a carboxy group can be easily introduced onto the surface of the base material of the medical material by ozone treatment or plasma treatment. Therefore, the functional group of $R_C$ in the monomer unit C is preferably an amino group, an isocyanate group, or an epoxy group from the viewpoint of ease of introduction of the copolymer onto the surface of the base material. This is because an amino group is capable of forming an amide bond with a carboxy group; an isocyanate group is capable of forming a urethane bond with a hydroxyl group; and an epoxy group is capable of forming an ether bond with a hydroxyl group.

From the viewpoint of reducing the steric hindrance due to the main chain by disposing the functional group at a position distant from the main chain of the copolymer to facilitate the reaction of the functional group with the base material, $R_C$ in the copolymer is more preferably an alkyl group substituted with at least one functional group selected from an amino group, an isocyanate group, and an epoxy group.

When the functional group of $R_C$ in the monomer unit C is an amino group, the amino group may be either an aliphatic amino group or an aromatic amino group. An aliphatic amino group is preferable because of its high reactivity. Examples of a monomer unit having an aliphatic amino group in the side chain include vinylamine, allylamine, alkyleneamine, p-aminoalkyl styrene, and aminoalkyl (meth)acrylate.

When the functional group of $R_C$ in the monomer unit C is a carboxy group, the carboxy group may be either an aliphatic carboxy group or an aromatic carboxy group. An aromatic carboxy group is preferable because of its high reactivity. Examples of a monomer unit having a carboxy group in the side chain include (meth)acrylic acid, 3-butenoic acid, and p-carboxystyrene. Among them, p-carboxystyrene having an aromatic carboxy group is preferable.

The copolymer preferably has a structure in which the monomer unit A, the monomer unit B, and the monomer unit C are randomly arranged rather than a structure in which the monomer arrangement is uneven as in a block copolymer. This is for the purpose of eliminating the unevenness in the monomer arrangement to prevent partial unevenness between hydrophilicity and hydrophobicity, and preventing the reaction of the coagulation system starting from the site of unevenness. A "block copolymer" refers to a copolymer having a molecular structure in which at least two kinds of polymers having different repeating units are covalently bonded together to form a long chain. "Randomly arranged" means that a copolymer is not a block copolymer.

Components other than the monomer unit A, the monomer unit B, and the monomer unit C may be copolymerized as long as the desired effect can be maintained. The total of mole fractions of the monomer unit A, the monomer unit B, and the monomer unit C based on all the monomer units that constitute the copolymer is preferably 70% or more, more preferably 80% or more. The upper limit of the total of mole fractions is 100%.

The mole fraction of the monomer unit A is preferably small enough to prevent destabilization of the structure of platelets or proteins due to too strong hydrophilicity of the copolymer as a whole, and is preferably large enough not to increase the hydrophobicity of the copolymer as a whole too much. Therefore, the mole fraction of the monomer unit A based on all the monomer units that constitute the copolymer is preferably 10 to 90%, more preferably 30 to 85%, still more preferably 45 to 80%.

The mole fraction of the monomer unit B is preferably small enough not to increase the hydrophobicity of the copolymer as a whole too much, and is preferably large enough not to lower the mobility of the copolymer as a whole. Therefore, the mole fraction of the monomer unit B based on all the monomer units that constitute the copolymer is preferably 10 to 90%, more preferably 20 to 75%, still more preferably 25 to 60%.

In addition, since many of the functional groups of $R_C$ in the monomer unit C have polarity, too large a mole fraction of the monomer unit C may destabilize the structure of platelets or proteins. For example, a polyethyleneimine homopolymer having an amino group is known to activate platelets. On the other hand, too small a mole fraction of the monomer unit C prevents immobilization of a sufficient amount of the copolymer onto the surface of the base material of the medical material so that the medical material may have insufficient antithrombotic properties. Therefore, the mole fraction of the monomer unit C based on all the monomer units that constitute the copolymer is preferably 0.5 to 40%, more preferably 1 to 25%, still more preferably 1.5 to 10%.

The mole fraction is calculated, for example, from the ratio of the peak area of each monomer unit to the peak area of all the monomer units that constitute the copolymer by nuclear magnetic resonance (NMR) measurement. If the mole fraction cannot be calculated by the NMR measurement for the reasons such as overlap of the peaks, the mole fraction may be calculated by elemental analysis.

The copolymer preferably has a number average molecular weight of 1,000 to 100,000. The number average molecular weight is preferably 1,000 or more, more preferably 2,000 or more, still more preferably 4,000 or more. This is because too small a number average molecular weight may not sufficiently exhibit an adhesion suppressing effect on platelets or proteins. Meanwhile, although the upper limit of the number average molecular weight of the copolymer is not particularly limited, too large a number average molecular weight may decrease the solubility. Therefore, the number average molecular weight is preferably 100,000 or less, more preferably 50,000 or less, still more preferably 20,000 or less. The number average molecular weight of the copolymer can be measured by gel permeation chromatography (GPC) as described below. Other monomers may also be copolymerized to the extent that they do not inhibit the action/function of the copolymer.

The copolymer is manufactured, for example, by the following manufacturing method, but the method is not limited thereto.

The monomers that constitute the copolymer, a polymerization solvent, and a polymerization initiator are mixed, and the mixture is stirred at a predetermined temperature for a predetermined period of time under a nitrogen atmosphere to cause a polymerization reaction. The reaction liquid is cooled to room temperature to stop the polymerization reaction, and the liquid is charged into a solvent such as hexane. The deposited precipitate is collected and dried under reduced pressure to give a copolymer.

The reaction temperature of the polymerization reaction is preferably 30 to 150° C., more preferably 50 to 100° C., still more preferably 70 to 80° C.

The pressure of the polymerization reaction is preferably normal pressure.

The reaction time of the polymerization reaction is appropriately selected according to the conditions such as the reaction temperature, and is preferably 1 hour or more, more preferably 3 hours or more, still more preferably 5 hours or more. When the reaction time is not too short, it is possible to prevent side reactions such as formation of a dimer, and to make the molecular weight control easier. On the other hand, the reaction time is preferably 24 hours or less, more preferably 12 hours or less. When the reaction time is not too long, it is possible to prevent the monomers from remaining after the polymerization reaction.

The polymerization solvent used in the polymerization reaction is not particularly limited as long as it is a solvent compatible with the monomers. Examples thereof include ether solvents such as dioxane and tetrahydrofuran, amide solvents such as N,N-dimethylformamide, sulfoxide solvents such as dimethylsulfoxide, aromatic hydrocarbon solvents such as benzene and toluene, alcohol solvents such as methanol, ethanol, isopropyl alcohol, amyl alcohol, and hexanol, and water. From the viewpoint of low toxicity, an alcohol solvent or water is preferably used.

The polymerization initiator for the polymerization reaction may be, for example, a photopolymerization initiator or a thermal polymerization initiator. A polymerization initiator that generates any of radicals, cations, and anions may be used. A radical polymerization initiator is preferably used because it hardly causes side reactions with the functional group of $R_C$ in the monomer unit C. Examples of the radical polymerization initiator include azo type initiators such as azobisisobutyronitrile, azobisdimethylvaleronitrile, and dimethyl azobis(isobutyrate), and peroxide initiators such as hydrogen peroxide, benzoyl peroxide, di-tert-butyl peroxide, and dicumyl peroxide.

The solvent into which the polymerization reaction solution is charged after stopping of the polymerization reaction is not limited as long as it is a solvent in which the copolymer precipitates. Examples of usable solvents include hydrocarbon solvents such as pentane, hexane, heptane, octane, nonane, and decane, and ether solvents such as dimethyl ether, ethyl methyl ether, diethyl ether, and diphenyl ether.

When the functional group of $R_C$ in the monomer unit C has high reactivity, the copolymer may be synthesized by capping the functional group with a protective group in advance, and deprotecting the functional group after polymerization.

The medical material contains the copolymer and a base material bonded to the copolymer.

The position of immobilization of the copolymer onto the base material is varied, and the copolymer may be distributed over the whole base material of the medical material or may be unevenly distributed on the surface of the base material. From the viewpoint of ease of manufacture of the medical material, the copolymer is preferably immobilized to be unevenly distributed on the surface of the base material.

The medical material is manufactured, for example, through formation of a bond by the functional group of $R_C$ in the monomer unit C of the copolymer with the functional group on the surface of the base material, and immobilization of the copolymer onto the base material. In the medical material, it is also possible that the copolymer is immobilized onto the base material through formation of a bond by the functional group of $R_C$ in the monomer unit C of the copolymer with another molecule, and formation of a bond by the molecule with the functional group on the surface of the base material.

"Forming a bond" means that the copolymer does not elute even when the medical material is cleaned with a solvent that dissolves the copolymer. Examples of the bond include a covalent bond, an ionic bond, and a coordination bond. A covalent bond is preferable because of high strength of the bond.

A "covalent bond" refers to a bond formed when atoms share electrons with each other. The covalent bond is a covalent bond between atoms of the copolymer and atoms on the surface of the base material such as carbon, nitrogen, oxygen, and sulfur atoms, and may be a single bond or a multiple bond. The kind of the covalent bond is not limited, and examples thereof include a disulfide bond, an amide bond, an azide bond, an ester bond, and a urethane bond. Among them, an amide bond is more preferable from the viewpoint of ease of forming a covalent bond and stability after bonding.

A "base material" refers to a component having the highest volume content among the components that constitute the medical material. The base material is not particularly limited, but a metal or a hydrophobic polymer is preferable as the base material from the viewpoint of imparting sufficient strength to the medical material.

The existence of the copolymer on the surface of the base material of the medical material can be confirmed by time-of-flight secondary ion mass spectrometry (TOF-SIMS) and X-ray photoelectron spectroscopy (XPS). When the composition of the surface of the base material is analyzed by TOF-SIMS measurement, carboxylate ions derived from vinyl carboxylate of the monomer unit B are detected. When XPS measurement is carried out, peaks of carbon atoms of the amide bond derived from the monomer unit A and carbon atoms of the ester group derived from vinyl carboxylate are detected in the C1s peaks showing the existence of carbon atoms. A "surface" refers to a portion up to a depth of 10 nm as measured by TOF-SIMS and XPS.

When the base material is made from a hydrophobic polymer, the base material is preferably made from, for example, a polyester-based polymer, expanded porous polytetrafluoroethylene (hereinafter referred to as "ePTFE"), polyurethane, polyether urethane, polyamide, a vinyl chloride-based polymer, polycarbonate, polystyrene, polyethylene, polypropylene, polymethylpentene, polymethyl methacrylate, or polyvinyl acetate. Among them, a polymer having an ester group such as a polyester-based polymer, polymethyl methacrylate, or polyvinyl acetate is preferable.

From the viewpoint of high general versatility, in the medical material according to a first preferable example, the base material is more preferably made from a polyester-based polymer, that is, a polymer having a repeating unit containing an ester bond in the main chain. Examples of the polyester-based polymer include polyethylene terephthalate (hereinafter referred to as "PET"), polytrimethylene terephthalate, polybutylene terephthalate, polyethylene naphthalate, and polybutylene naphthalate. Among them, PET is more preferable as a base material of an antithrombotic material because it is high in general versatility. The "polyester-based polymer" means a polymer having a repeating unit containing an ester bond in the main chain.

A "hydrophobic polymer" refers to a polymer having a solubility of 0.1 g or less in 100 g of pure water at 20° C. with the number average molecular weight of the polymer being 1,000 or more and 50,000 or less.

For example, when the hydrophobic polymer has a functional group such as a urethane group, it is possible to covalently bond the functional group to a copolymer comprising the monomer unit C having a hydroxyl group or the like and immobilize the copolymer onto the surface of the base material.

Even when the hydrophobic polymer has no functional group, it is similarly possible to immobilize the copolymer onto the surface of the base material by treating the surface of the base material with plasma, corona or the like to introduce a functional group onto the surface.

Moreover, in a base material made from a polyester-based polymer, although not particularly limited, the following method can be employed. That is, an ester bond on the surface of the base material is hydrolyzed by an acid or alkali treatment, and a carboxyl group that appears on the surface of the base material and the functional group of $R_C$ in the monomer unit C of the copolymer are subjected to a condensation reaction to be covalently bonded together. In this example, if the functional group of $R_C$ in the monomer unit C is an amino group, the amino group forms an amide bond to covalently bond the copolymer to the base material. In these methods, the copolymer may be brought into contact with the surface of the base material for the reaction, or alternatively, the copolymer dissolved in a solvent may be brought into contact with the surface of the base material for the reaction.

It is more preferable to hydrolyze and oxidize the surface of the base material made from the polyester-based polymer. Hydrolysis and oxidation of the surface of the base material made from the polyester-based polymer cause hydrolysis and oxidation of the ester bond so that the copolymer is more easily immobilized. A specific example of a preferable method of hydrolysis and oxidation is a method of treating the surface of the base material with an acid or an alkali and an oxidizing agent. The method of hydrolysis and oxidation may be carried out only with use of an acid or an alkali. However, the method of treating the surface of the base material with an acid or an alkali and an oxidizing agent is particularly preferably employed for the purpose of increasing the introduction amount of the copolymer to improve the antithrombotic properties. This is because such a method is capable of preventing mixing of hydroxyl groups and carboxyl groups generated by hydrolysis of the ester bond, efficiently promoting a condensation reaction with the functional group of $R_C$ in the monomer unit C of the copolymer, and further reducing the existing hydroxyl groups to prevent activation of the complement upon contact of the medical material with the blood.

A preferable combination of agents in the step of hydrolyzing and oxidizing the ester bond on the surface of the base material made from the polyester-based polymer with an acid or an alkali and an oxidizing agent is a combination of an acid and an oxidizing agent. It is also possible to treat the surface of the base material with an alkali, and then treat the surface with an acid and an oxidizing agent.

The kind of the acid used is not particularly limited, and examples thereof include inorganic acids such as hydrochloric acid, hydrobromic acid, hydroiodic acid, hypochlorous acid, chlorous acid, perchloric acid, sulfuric acid, fluorosulfonic acid, nitric acid, phosphoric acid, hexafluoroantimonic acid, tetrafluoroboric acid, chromic acid, and boric acid, sulfonic acids such as methanesulfonic acid, ethanesulfonic acid, benzenesulfonic acid, p-toluenesulfonic acid, trifluoromethanesulfonic acid, and sodium polystyrene sulfonate, carboxylic acids such as acetic acid, citric acid, formic acid, gluconic acid, lactic acid, oxalic acid, and tartaric acid, vinylic carboxylic acids such as ascorbic acid and meldrum acid, and nucleic acids such as deoxyribonucleic acid and ribonucleic acid. Among them, hydrochloric acid, sulfuric acid and the like are more preferable from the viewpoint of handleability and the like.

The kind of the base used is not particularly limited, and examples thereof include alkali metal hydroxides such as lithium hydroxide, sodium hydroxide, potassium hydroxide, rubidium hydroxide, and cesium hydroxide, tetraalkylammonium hydroxides such as tetramethylammonium hydroxide and tetraethylammonium hydroxide, alkaline earth metal hydroxides such as calcium hydroxide, strontium hydroxide, barium hydroxide, europium hydroxide, and thallium hydroxide, guanidine compounds, hydroxides of ammine complexes such as diamminesilver(I) hydroxide and tetraamminecopper(II) hydroxide, trimethylsulfonium hydroxide, and diphenyliodonium hydroxide. Among them, lithium hydroxide, sodium hydroxide, potassium hydroxide and the like are more preferable from the viewpoint of handleability and the like.

The kind of the oxidizing agent used is not particularly limited, and examples thereof include halogens such as potassium nitrate, hypochlorous acid, chlorous acid, perchloric acid, fluorine, chlorine, bromine, and iodine, permanganate salts such as potassium permanganate, sodium permanganate trihydrate, ammonium permanganate, silver permanganate, zinc permanganate hexahydrate, magnesium permanganate, calcium permanganate, and barium permanganate, peroxides such as cerium ammonium nitrate, chromic acid, dichromic acid, and hydrogen peroxide water, Tollens' reagent, and sulfur dioxide. Among them, permanganate salts are more preferable from the viewpoint of the strength of the oxidizing agent and that they are capable of moderately preventing the deterioration of the material.

The medical material according to a second preferable example further contains a phosphonic acid derivative or a catechol derivative, the base material is made of a metal, the copolymer is bonded to the phosphonic acid derivative or the catechol derivative, the phosphonic acid derivative is bonded to the base material via a phosphonic acid group thereof, and the catechol derivative is bonded to the base material via a catechol group thereof. In other words, in the medical material according to the second preferable example, the medical material contains the above-mentioned copolymer, a phosphonic acid derivative or a catechol derivative, and a base material made of a metal, the copolymer is bonded to the phosphonic acid derivative or the catechol derivative, the phosphonic acid derivative is bonded to the base material via a phosphonic acid group thereof, and the catechol derivative is bonded to the base material via a catechol group thereof.

A "metal" refers to a material containing a metal element. Specifically, the metal used is preferably selected from the group consisting of iron, titanium, aluminum, tin, gold, silver, copper, platinum, chromium, cobalt, nickel, zinc, tungsten, magnesium, tantalum, and alloys, metal oxides, and metal hydroxides thereof. Among them, a metal selected from the group consisting of stainless steel, a cobalt-chromium alloy, a nickel-titanium alloy, tantalum, titanium, a titanium alloy, and a magnesium alloy, which is known to have high biocompatibility, is more preferable. Although the shape of the metal is not particularly limited, the shape may be, for example, a plate, a sheet, a rod, a wire, a powder including fine particles, and a thin film.

In a base material made of a metal, the method of immobilizing the copolymer is not particularly limited, but it is preferable that the copolymer be bonded to the phosphonic acid derivative or the catechol derivative, the phosphonic acid derivative be bonded to the base material via a phosphonic acid group thereof, and the catechol derivative be bonded to the base material made of a metal via a catechol group thereof. This is because this method enables introduction of the copolymer onto the metal surface at high density. More specifically, in a metal and a phosphonic acid group, it is preferable that a metal atom and a phosphorus atom be covalently bonded via an oxygen atom (metal-O—P), and in a metal and a catechol group, it is preferable that a metal atom and a carbon atom in a benzene ring be covalently bonded via an oxygen atom (metal-O-Ph).

Of these, the phosphonic acid derivative is preferably used because it has strong inter-action between molecules (for example, van der Waals force, and hydrophilic and hydrophobic interactions), and has high resistance to ultrasonic cleaning using a good solvent and immersion in a phosphate buffer simulating a physiological environment so that it is difficult to desorb.

The phosphonic acid derivative is a compound represented by chemical formula (V), and has a phosphonic acid group at one end of an alkyl group and an arbitrary functional group at the other end thereof:

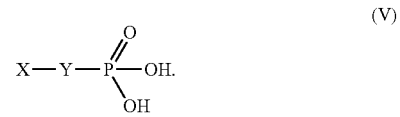

(V)

Preferable specific examples of X and Y in the chemical formula (V) are shown below.

X is preferably a highly reactive functional group for the purpose of immobilizing other substances or the like. Preferable specific examples thereof include an amino group, a carboxy group, an aldehyde group, a hydroxyl group, a thiol group, an isocyanate group and a thioisocyanate group, an epoxy group, a halogenated alkyl group, and a vinyl group. This makes it possible to arrange a highly reactive functional group of the phosphonic acid derivative on the metal surface so that it is possible to immobilize the copolymer at high density. In the case where the functional group of $R_C$ in the monomer unit C is an amino group, X is preferably a carboxy group since it can form an amide group with the amino group.

Furthermore, Y is preferably an alkylene group having 5 to 20 carbon atoms (a part or all of the hydrogen atoms on the alkylene group are optionally substituted with fluorine atoms). Y is preferably an alkylene group having 5 or more carbon atoms because the intermolecular force in the phosphonic acid derivative strongly acts to facilitate increase in the surface density. Y is preferably an alkylene group having 20 or less carbon atoms because it is not difficult to synthesize and handle the phosphonic acid derivative.

For the above-mentioned reasons, the phosphonic acid derivative is, for example, preferably carboxyalkylphosphonic acid or aminoalkylphosphonic acid, and is more preferably carboxyalkylphosphonic acid. The number of the carbon atoms of the carboxyalkylphosphonic acid derivative is not particularly limited. For example, compounds represented by general formulae (VI) and (VII) can be mentioned:

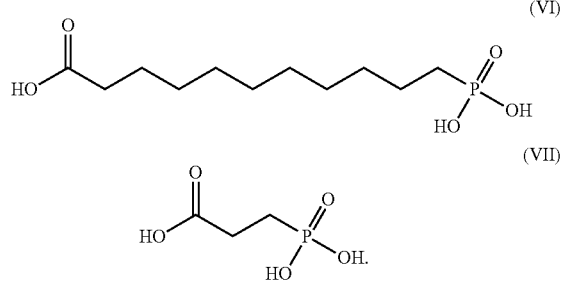
(VI)
(VII)

The catechol derivative is an organic compound in which a catechol group represented by general formula (VIII) is bonded to a carbon atom in the compound:

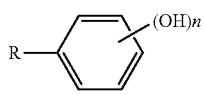
(VIII)

wherein n represents an integer of 2 to 5.

R is an alkyl group having a reactive functional group at an end. The alkyl group may contain an amide bond or an ester bond.

The catechol derivative is not particularly limited as long as it is a compound in which a catechol group represented by general formula (VIII) is bonded to a carbon atom in the compound. Specific examples of the structure of the compound include general formulae (IX) to (XII):

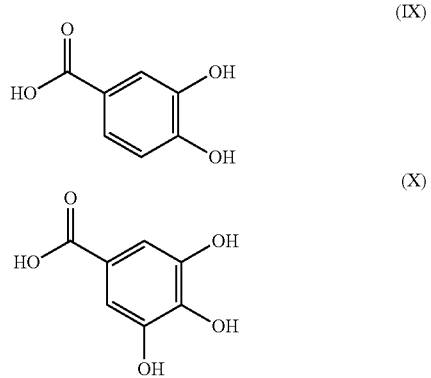
(IX)
(X)

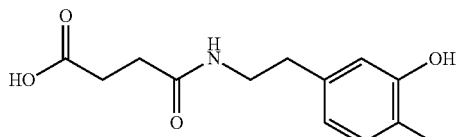
(XI)

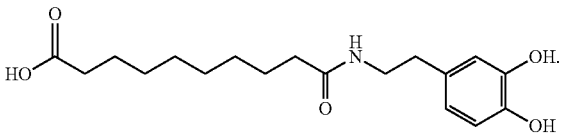
(XII)

It is preferable to clean the metal surface before immobilizing the phosphonic acid derivative or the catechol derivative onto the surface. This is because it is possible to remove adsorbed substances that inhibit the immobilization of the phosphonic acid derivative or the catechol derivative such as carbon dioxide, water and organic substances, and to facilitate the immobilization of the phosphonic acid derivative or the catechol derivative. Examples of the cleaning method include ultrasonic cleaning in an organic solvent, Ar etching, and ultraviolet irradiation. Moreover, a plurality of cleaning methods may be combined. Furthermore, it is preferable to clean the metal surface with a scouring solution in the cleaning method. Since the scouring solution is a mixed solution of hydrogen peroxide and sulfuric acid and has extremely strong oxidizing power, it can not only remove more organic substances on the metal surface, but can also increase the amount of hydroxyl groups on the metal surface to increase the immobilization amount of the phosphonic acid derivative.

Examples of the method of covalently bonding the phosphonic acid derivative or the catechol derivative to the metal surface include the following methods. A metal material is immersed in a solution of the phosphonic acid derivative or the catechol derivative in tetrahydrofuran (hereinafter referred to as "THF") at room temperature, and then the solution is concentrated using an evaporator and then dried under vacuum. The solution is heated at 120° C., allowed to stand to cool, ultrasonically cleaned with methanol, cleaned with water, and then dried under vacuum. Alternatively, a cleaned metal material is immersed in an ethanol solution of the phosphonic acid derivative or the catechol derivative at 37° C. overnight, then cleaned with ethanol and water, and then dried under vacuum.

Then, the copolymer is covalently bonded to the phosphonic acid derivative or the catechol derivative. Specifically, when the phosphonic acid derivative is used, the functional group of $R_C$ in the monomer unit C and the phosphonic acid group of the phosphonic acid derivative are covalently bonded together, and when the catechol derivative is used, the functional group of $R_C$ in the monomer unit C and the catechol group of the catechol derivative are covalently bonded together. In this way, the copolymer can be immobilized onto the metal surface.

The existence of the phosphonic acid derivative on the metal surface is confirmed by at least one peak selected from the group consisting of $^{31}P^-$ peak, $^{47}PO^-$ peak, $^{63}PO_2^-$ peak, $^{79}PO_3^-$ peak, $^{94}CH_3PO_3^-$ peak, $^{107}C_2H_4PO_3^-$ peak, and $^{265}C_{11}H_{22}PO_5^-$ peak of negative secondary ions, and $^{65}PH_2O_2^+$ peak, $^{82}PH_3O_3^+$ peak, $^{96}CH_5PO_3^+$ peak, $^{249}C_{11}H_{22}PO_4^+$ peak, and $^{277}C_{12}H_{22}PO_5^+$ peak of positive secondary ions that are observed by TOF-SIMS.

The existence of the catechol derivative on the metal surface is confirmed by at least one peak selected from the group consisting of $^{98}C_4H_4NO_2^-$ peak, $^{116}C_4H_6NO_3^-$ peak, $^{122}C_7H_6O_2^-$ peak, $^{135}C_8H_7O_2^-$ peak, and $^{252}C_{12}H_{14}NO_5^-$ peak of negative secondary ions, and $^{137}C_8H_9O_2^+$ peak, $^{154}C_8H_{12}NO_2^+$ peak, $^{208}C_{12}H_{18}NO_2^+$ peak, and $^{254}C_{12}H_{16}NO_5^+$ peak of positive secondary ions that are observed by GCIB-TOF-SIMS.

In a base material made of a metal, the base material can be preferably used in a medical device made of a metal material required to have antithrombotic properties, specifically, an indwelling medical device such as a stent, a stent graft, and a thrombus capture device.

A method of chemically reacting a carboxy group, an amino group, or a hydroxyl group of the phosphonic acid derivative or the catechol derivative bonded to the metal, a carboxy group introduced by hydrolysis of the polyester-based polymer, or a hydroxyl group or a carboxyl group introduced into a part of a vinyl chloride-based polymer described later with the functional group of $R_C$ in the monomer unit C of the copolymer may be a method of condensation reaction using a dehydration condensation agent or the like.

The kind of the dehydration condensation agent used is not particularly limited, and examples thereof include carbodiimide compounds such as N,N'-dicyclohexylcarbodiimide, N,N'-diisopropylcarbodiimide, 1-ether-3-(3-dimethylaminopropyl) carbodiimide, 1-ether-3-(3-dimethylaminopropyl) carbodiimide hydrochloride (hereinafter referred to as "EDC"), 1,3-bis(2,2-dimethyl-1,3-dioxolan-4-ylmethyl) carbodiimide, N-{3-(dimethylamino)propyl-}-N'-ethylcarbodiimide, N-{3-(dimethylamino)propyl-}-N'-ethylcarbodiimide methiodide, N-tert-butyl-N'-ethylcarbodiimide, N-cyclohexyl-N'-(2-morpholinoethyl) carbodiimide meso-p-toluenesulfonate, N,N'-di-tert-butylcarbodiimide, and N,N'-di-p-tricarbodiimide, and triazine compounds such as 4(-4,6-dimethoxy-1,3,5-triazin-2-yl)-4-methyl morpholinium chloride n hydrate (hereinafter referred to as "DMT-MM").

The dehydration condensation agent may be used together with a dehydration condensation accelerator. The dehydration condensation accelerator used is not particularly limited, and examples thereof include pyridine, 4-dimethylaminopyridine (hereinafter referred to as "DMAP"), triethylamine, isopropylamine, 1-hydroxybenzotriazole, and N-hydroxysuccinimide.

The copolymer, the metal- or polyester-based polymer, the dehydration condensation agent, and the dehydration condensation accelerator may be reacted in the form of a mixed aqueous solution, or may be added in order and subjected to the reaction.

The immobilization amount of the copolymer onto the surface of the base material can be calculated by XPS measurement. Specifically, an N1 s peak indicating the existence of nitrogen atoms derived from the amide group of the monomer unit A is observed around a binding energy value of 396 eV to 403 eV. The ratio of the N1s peak area to the total peak area is preferably 1.0 to 20.0 at %, more preferably 1.5 to 12.0 at %, still more preferably 3.0 to 10.0 at %. If the immobilization amount of the copolymer is small, the medical material has insufficient antithrombotic properties, whereas if the immobilization amount is too large, platelets and proteins may be trapped in the molecular chain of the copolymer. The abundance rate of nitrogen atoms to all the atoms is calculated by rounding off the rate to one decimal place.

In the medical material according to a third preferable example, the base material is made from a polymer a part of which contains a hydroxyl group or a carboxy group introduced therein and in which at least one hydrogen atom in the main chain is substituted with a chlorine atom, or a polymer a part of which contains a hydroxyl group or a carboxy group introduced therein and that has a siloxane bond in at least a part thereof, and the copolymer is bonded to the base material via the hydroxyl group or the carboxy group. That is, in the third preferable example, the medical material contains the copolymer, and the base material made from a vinyl chloride-based polymer a part of which contains a hydroxyl group or a carboxy group introduced therein, or the base material made from a silicone-based polymer a part of which contains a hydroxyl group or a carboxy group introduced therein, and the copolymer is bonded to the base material via the hydroxyl group or the carboxy group.

The "vinyl chloride-based polymer" means a polymer in which at least one hydrogen atom in the main chain is substituted with a chlorine atom, and examples thereof include polyvinyl chloride, polyvinylidene chloride, and polytetrachloroethylene. Moreover, other monomers may be copolymerized as long as the performance of the vinyl chloride-based polymer is not disturbed. The "silicone-based polymer" means a polymer having a siloxane bond in at least a part thereof.

In the third preferable example, it is preferable that a hydroxyl group or a carboxy group be introduced into a part of the base material made from the vinyl chloride-based polymer to cause a condensation reaction with the functional group of $R_C$ in the monomer unit C of the copolymer for covalent bonding.

There are various methods of producing the medical material containing the vinyl chloride-based polymer as the base material. An example of the method is a method of coating a surface of the base material with a copolymer comprising a monomer unit having a hydroxyl group or a carboxy group and a vinyl chloride-based monomer unit, and causing a condensation reaction with the functional group of $R_C$ to immobilize the copolymer. Alternatively, the medical material can also be obtained by covalently bonding a copolymer comprising a monomer unit having a hydroxyl group or a carboxyl group and a vinyl chloride-based monomer unit with a copolymer having $R_C$ in advance to synthesize a graft polymer, and coating the base material made from the vinyl chloride-based polymer with the graft polymer. Examples of the monomer unit having a hydroxyl group or a carboxy group include vinyl alcohol, acrylic acid, methacrylic acid, and 2-hydroxyethyl methacrylate.

The medical material can be preferably used in medical devices (for example, artificial kidneys, artificial lungs, artificial blood vessels, artificial valves, stents, stent grafts, catheters, thrombus capture devices, angioscopes, suture threads, blood circuits, tubes, cannulas, blood bags, and syringes). It is particularly preferable that the medical material be used in a thrombus capture device.

The thrombus capture device includes the medical material. The thrombus capture device preferably employs the medical material according to the first preferable example or the second preferable example. Since the thrombus capture device comes into contact with the blood at a high shear rate, the device preferably includes a base material bonded to the copolymer, or includes the copolymer, the phosphonic acid derivative or the catechol derivative, and the base material made of a metal.

A "thrombus capture device" refers to a medical device including a filter made of a mesh or a porous film for capturing free thrombi. The material of the base material, that is, the material of the filter is preferably stainless steel, a cobalt-chromium alloy, a nickel-titanium alloy, tantalum, titanium, a titanium alloy and a magnesium alloy, a polyester-based polymer, polyalkyl (meth)acrylate, polyurethane, a vinyl chloride-based polymer, polycarbonate, or polytetrafluoroethylene. In particular, a polyester-based polymer, particularly PET is preferable because of its high flexibility and in vivo stability. These materials can be used singly or in combination of two or more kinds thereof.

When the filter has a mesh shape to capture free thrombi more accurately, the single yarn diameter of the fiber that constitutes the mesh is preferably 10 to 50 μm, more preferably 20 to 40 μm. In addition, the mesh opening is preferably 10 to 200 μm, more preferably 50 to 150 μm.

In the thrombus capture device, it is important to improve the antithrombotic properties of the filter since the shear rate of the blood is the highest and the turbulence of the blood tends to occur at the filter.

Figure 2:
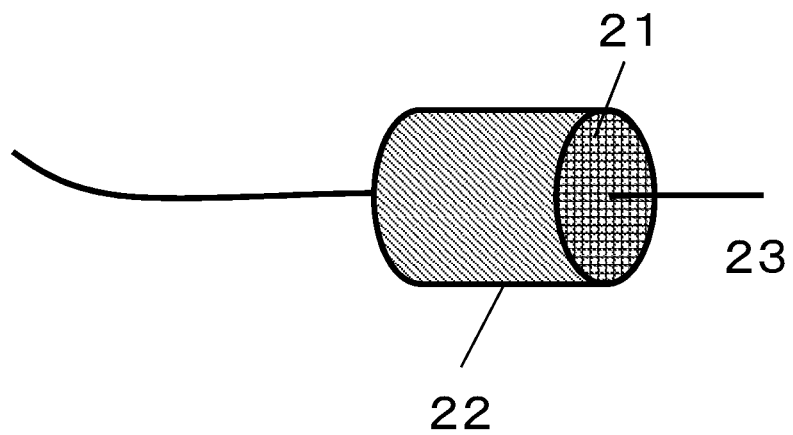
FIG. 2 shows the thrombus capture device according to a second example, the device including our copolymer.

Examples of the form of the thrombus capture device include a form including, as in a first thrombus capture device shown in FIG. 1, a filter 11 processed into a bag shape, a ring-shaped part 12 and a support line part 13 for maintaining the shape of the filter, and a core part 14, and a form including, as in a second thrombus capture device shown in FIG. 2, a filter 21, a cylindrical support part 22, and a core part 23.

The ring-shaped part 12, the support line part 13, the core part 14, the cylindrical support part 22, and the core part 23 are not particularly limited, but stainless steel, a cobalt-chromium alloy, a nickel-titanium alloy, tantalum, titanium, a titanium alloy and a magnesium alloy, a polyester-based polymer, polyalkyl (meth)acrylate, polyurethane, a vinyl chloride-based polymer and polycarbonate, and polytetrafluoroethylene are preferable.

It is possible to assemble the thrombus capture device into the form shown in FIG. 1 or 2 after immobilizing the copolymer onto the filter. Alternatively, it is also possible to assemble the thrombus capture device into the form and then immobilize the copolymer onto the filter.

The blood circuit includes the medical material according to the third preferable aspect. A "blood circuit" is a tube through which blood flows during the treatment by extracorporeal blood circulation, and is used by being connected to an artificial kidney or an artificial lung. The operating time of the blood circuit varies according to the kind of treatment, but the blood circuit may be used continuously for several days. Therefore, the blood circuit is required to have potent antithrombotic properties.

The base material of the blood circuit is preferably made from a vinyl chloride-based polymer or a silicone-based polymer. A vinyl chloride-based polymer is more preferable because it is high in general versatility. Therefore, the medical material according to the third preferable example is preferably used.

EXAMPLES

Hereinafter, our copolymers, medical materials and methods will be described with reference to experimental examples, but this disclosure is not limited to the experimental examples.

Evaluation Methods (1) NMR Measurement

In 2 ml of chloroform-D, 99.7% (containing 0.05 v/v % TMS, manufactured by Wako Pure Chemical Industries, Ltd.), 2 mg of a copolymer was dissolved, and the solution was put in an NMR sample tube and subjected to NMR measurement (superconducting FTNMR EX-270 manufactured by JEOL Ltd.). The temperature was room temperature, and the cumulated number was 32 times.

(2) Number Average Molecular Weight

A 0.1 N $LiNO_3$ solution of water/methanol=50/50 (volume ratio) was adjusted and used as a GPC developing solution. In 2 ml of this solution, 2 mg of a copolymer was dissolved. Into Prominence GPC system manufactured by SHIMADZU CORPORATION, 100 μL of the solution was poured and subjected to the measurement. The device configuration was as follows:

Pump: LC-20AD
Autosampler: SIL-20AHT
Column oven: CTO-20A
Column: GMPWXL (7.8 mm (internal diameter)×30 cm, particle size: 13 μm) manufactured by Tosoh Corporation.

The flow rate was 0.5 mL/min, and the measurement time was 30 minutes. The detection was performed with a differential refractive index detector RID-10A (manufactured by SHIMADZU CORPORATION), and the number average molecular weight of the copolymer was calculated from the peak derived from the copolymer that appeared around the elution time of 15 minutes. The number average molecular weight of the copolymer was calculated by rounding off the number to the nearest hundred. A polyethylene oxide standard sample (0.1 kD to 1258 kD) manufactured by Agilent was used to prepare a calibration curve.

(3) XPS Measurement

A medical material (for example, a PET mesh) containing an immobilized copolymer was cut into a size of 1 cm in width and 1 cm in length. The abundance rate of nitrogen atoms to all the atoms on the surface of the medical material was calculated by XPS measurement under the following conditions.

Measurement Conditions
Apparatus: ESCALAB 220iXL (manufactured by VG Scientific Ltd.)
Excited X-ray: monochromatic Al K $\alpha$1,2 ray (1486.6 eV)
X-ray diameter: 1 mm
X-electron take-off angle: 90° (inclination of the detector with respect to the surface of the medical material)

(4) Blood Coagulation Test

A lid of a polyethylene centrifuge tube (manufactured by AS ONE Corporation) was used as a test vessel. A medical material cut into an appropriate size was placed in the test vessel, then 1 mL of human blood not containing any anticoagulant drug was added thereto, and the test vessel was shaken at 100 rpm for 30 minutes. The medical material was collected and cleaned with physiological saline for 10 seconds. Then, the percentage of the area where thrombi adhered in the area of the whole surface of the collected medical material was calculated. The percentage of the area where thrombi adhered was determined by binarizing the image of the collected medical material into white or black, and calculating the percentage of the black area.

(5) Blood Circulation Test

Figure 3:
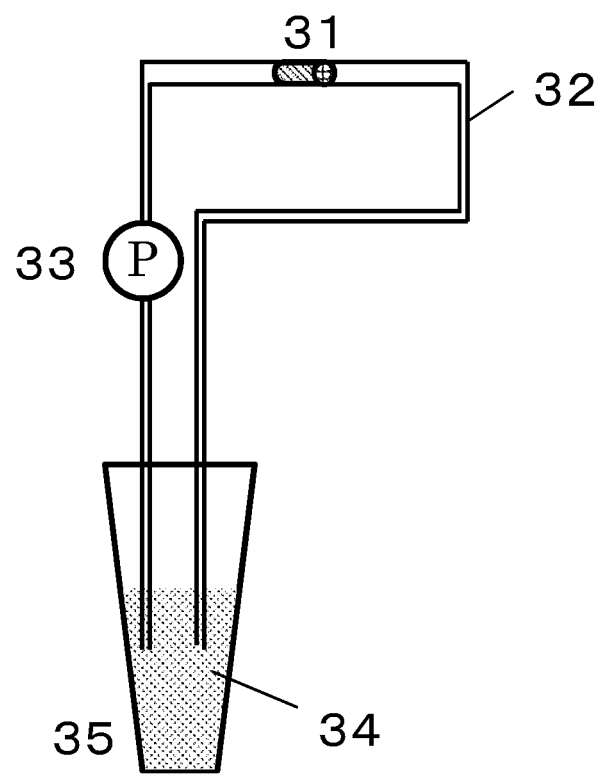
FIG. 3 is a schematic diagram of a blood circulation test.

Both ends of a polypropylene micro test tube (manufactured by Eppendorf Co., Ltd., volume: 0.5 mL) were cut so that the micro test tube would have a columnar shape of 1 cm in length, and a PET mesh was adhered to one side of the micro test tube with an instantaneous adhesive to prepare a thrombus capture device. As shown in FIG. 3, a test system including a thrombus capture device 31, a blood circuit 32 made of vinyl chloride, a pump 33, and a centrifuge tube 35 for storing blood 34 was assembled, and 24 mL of human blood to which heparin was added to have a concentration of 0.5 U/mL was circulated in the test system at a flow rate of 50 mL/min for 60 minutes. The PET mesh was collected, and the percentage of the area where thrombi adhered in the area of the whole surface of the collected PET mesh was calculated in the same manner as in the blood coagulation test.

Method of Manufacturing Copolymer

Example 1

All of the monomer, polymerization solvent, and polymerization initiator used were manufactured by Tokyo Chemical Industry Co., Ltd. That is, 19.5 g of vinylpyrrolidone, 17.5 g of vinyl propanoate, 1.0 g of allylamine hydrochloride, 56 g of t-amyl alcohol as a polymerization solvent, and 0.175 g of 2,2'-azobis(2,4-dimethylvaleronitrile) as a polymerization initiator were mixed, and the mixture was stirred at 80° C. for 6 hours under a nitrogen atmosphere. The reaction liquid was cooled to room temperature to stop the reaction and charged into hexane. The deposited white precipitate was collected and dried under reduced pressure at 20° C. for 12 hours. Then, the copolymer was dissolved in an aqueous solution of sodium hydrogen carbonate (manufactured by Wako Pure Chemical Industries, Ltd.) adjusted to pH 8 to remove hydrochloric acid, and moisture was removed using an evaporator to give a vinylpyrrolidone/vinyl propanoate/allylamine random copolymer.

From the measurement results of $^1$H-NMR, the mole fractions of vinylpyrrolidone, vinyl propanoate, and allylamine to all the constituent monomer units were 72.0%, 25.0%, and 3.0%, respectively. In addition, the number average molecular weight of the copolymer calculated from the measurement result of GPC was 4,300. The copolymer was designated as Copolymer A.

Example 2

A vinylpyrrolidone/vinyl propanoate/allylamine random copolymer was obtained by the same synthesis procedure as that for Copolymer A except that the charged amount of allylamine hydrochloride was changed to 0.33 g.

From the measurement results of $^1$H-NMR, the mole fractions of vinylpyrrolidone, vinyl propanoate, and allylamine to all the constituent monomer units were 58.8%, 40.0%, and 1.2%, respectively. In addition, the number average molecular weight of the copolymer calculated from the measurement result of GPC was 11,000. The copolymer was designated as Copolymer B.

Example 3

A vinylpyrrolidone/vinyl propanoate/allylamine random copolymer was obtained by the same synthesis procedure as that for Copolymer A except that the charged amount of allylamine hydrochloride was changed to 2.33 g.

From the measurement results of $^1$H-NMR, the mole fractions of vinylpyrrolidone, vinyl propanoate, and allylamine to all the constituent monomer units were 48.0%, 20.0%, and 32.0%, respectively. In addition, the number average molecular weight of the copolymer calculated from the measurement result of GPC was 2,700. The copolymer was designated as Copolymer C.

Example 4

All of the monomer, polymerization solvent, and polymerization initiator used were manufactured by Tokyo Chemical Industry Co., Ltd. That is, 4.1 g of N-vinylacetamide, 15.0 g of vinyl pivalate, 0.18 g of allylamine hydrochloride, 30 g of t-amyl alcohol as a polymerization solvent, and 0.107 g of 2,2'-azobis(2,4-dimethylvaleronitrile) as a polymerization initiator were mixed, and the mixture was stirred at 80° C. for 6 hours under a nitrogen atmosphere. The reaction liquid was cooled to room temperature to stop the reaction and charged into hexane. The deposited white precipitate was collected and dried under reduced pressure at 20° C. for 12 hours. Then, the copolymer was dissolved in an aqueous solution of sodium hydrogen carbonate (manufactured by Wako Pure Chemical Industries, Ltd.) adjusted to pH 8 to remove hydrochloric acid, and moisture was removed using an evaporator to give an N-vinylacetamide/vinyl pivalate/allylamine random copolymer.

From the measurement results of $^1$H-NMR, the mole fractions of N-vinylacetamide, vinyl pivalate, and allylamine to all the constituent monomer units were 48.0%, 50.0%, and 2.0%, respectively. In addition, the number average molecular weight of the copolymer calculated from the measurement result of GPC was 4,600. The copolymer was designated as Copolymer D.

Example 5

All of the monomer, polymerization solvent, and polymerization initiator used were manufactured by Tokyo Chemical Industry Co., Ltd. That is, 18.7 g of vinylpyrrolidone, 18.3 g of vinyl myristate, 0.18 g of allylamine hydrochloride, 56 g of t-amyl alcohol as a polymerization solvent, and 0.120 g of 2,2'-azobis(2,4-dimethylvaleronitrile) as a polymerization initiator were mixed, and the mixture was stirred at 80° C. for 6 hours under a nitrogen atmosphere. The reaction liquid was cooled to room temperature to stop the reaction and charged into hexane. The deposited white precipitate was collected and dried under reduced pressure at 20° C. for 12 hours. Then, the copolymer was dissolved in an aqueous solution of sodium hydrogen carbonate (manufactured by Wako Pure Chemical Industries, Ltd.) adjusted to pH 8 to remove hydrochloric acid, and moisture was removed using an evaporator to give an N-vinylpyrrolidone/vinyl myristate/allylamine random copolymer.

From the measurement results of $^1$H-NMR, the mole fractions of vinylpyrrolidone, vinyl myristate, and allylamine to all the constituent monomer units were 78.0%, 20.0%, and 2.0%, respectively. In addition, the number average molecular weight of the copolymer calculated from the measurement result of GPC was 3,800. The copolymer was designated as Copolymer E.

Example 6

All of the monomer, polymerization solvent, and polymerization initiator used were manufactured by Tokyo Chemical Industry Co., Ltd. That is, 9.5 g of vinylpyrrolidone, 9.5 g of vinyl propanoate, 0.7 g of 2-isocyanatoethyl acrylate, 40 g of tetrahydrofuran as a polymerization solvent, and 0.1 g of 2,2'-azobis(2,4-dimethylvaleronitrile) as a polymerization initiator were mixed, and the mixture was stirred at 70° C. for 5 hours under a nitrogen atmosphere. The reaction liquid was cooled to room temperature to stop the reaction and charged into hexane. The deposited white precipitate was collected and dried under reduced pressure at 20° C. for 12 hours to give a vinylpyrrolidone/vinyl propanoate/2-isocyanatoethyl acrylate random copolymer.

From the measurement results of $^1$H-NMR, the mole fractions of vinylpyrrolidone, vinyl propanoate, and 2-isocyanatoethyl acrylate to all the constituent monomer units were 75.0%, 23.0%, and 2.0%, respectively. In addition, the number average molecular weight of the copolymer calculated from the measurement result of GPC was 3,500. The copolymer was designated as Copolymer F.

Example 7

A vinylpyrrolidone/vinyl propanoate/glycidyl methacrylate random copolymer was obtained by the same synthesis procedure as that for Copolymer F except that glycidyl methacrylate was used instead of 2-isocyanatoethyl acrylate.

From the measurement results of $^1$H-NMR, the mole fractions of vinylpyrrolidone, vinyl propanoate, and glycidyl methacrylate to all the constituent monomer units were 71.0%, 26.0%, and 3.0%, respectively. In addition, the number average molecular weight of the copolymer calculated from the measurement result of GPC was 15,200. The copolymer was designated as Copolymer G.

Comparative Example 1

First, 19.5 g of vinylpyrrolidone, 17.5 g of vinyl propanoate, 56 g of t-amyl alcohol as a polymerization solvent, and 0.175 g of 2,2'-azobis(2,4-dimethylvaleronitrile) as a polymerization initiator were mixed, and the mixture was stirred at 80° C. for 6 hours under a nitrogen atmosphere. The reaction liquid was cooled to room temperature to stop the reaction and charged into hexane. The deposited white precipitate was collected and dried under reduced pressure at 20° C. for 12 hours to give a vinylpyrrolidone/vinyl propanoate random copolymer.

From the measurement results of $^1$H-NMR, the mole fractions of vinylpyrrolidone and vinyl propanoate to all the constituent monomer units were 60.0% and 40.0%, respectively. In addition, the number average molecular weight of the copolymer calculated from the measurement result of GPC was 12,500. The copolymer was designated as Copolymer F. Copolymer H does not comprise the monomer unit C.

Comparative Example 2

A vinylpyrrolidone/vinyl propanoate/allylamine random copolymer was obtained by the same synthesis procedure as that for Copolymer A except that the charged amount of allylamine hydrochloride was changed to 8.33 g.

From the measurement results of $^1$H-NMR, the mole fractions of vinylpyrrolidone, vinyl propanoate, and allylamine to all the constituent monomer units were 37.0%, 18.0%, and 45.0%, respectively. In addition, the number average molecular weight of the copolymer calculated from the measurement result of GPC was 1,200. The copolymer was designated as Copolymer I.

Comparative Example 3

A vinylpyrrolidone/vinyl propanoate/allylamine random copolymer was obtained by the same synthesis procedure as that for Copolymer A except that the charged amount of allylamine hydrochloride was changed to 0.03 g.

From the measurement results of $^1$H-NMR, the mole fractions of vinylpyrrolidone, vinyl propanoate, and allylamine to all the constituent monomer units were 56.0%, 43.6%, and 0.4%, respectively. In addition, the number average molecular weight of the copolymer calculated from the measurement result of GPC was 10,600. The copolymer was designated as Copolymer J.

Comparative Example 4

First, 10.8 g of vinylpyrrolidone, 11.5 g of vinyl acetate, 1.0 g of allylamine hydrochloride, 56 g of t-amyl alcohol as a polymerization solvent, and 0.175 g of 2,2'-azobis(2,4-dimethylvaleronitrile) as a polymerization initiator were mixed, and the mixture stirred at 70° C. for 6 hours under a nitrogen atmosphere. The reaction liquid was cooled to room temperature to stop the reaction and charged into hexane. The deposited white precipitate was collected and dried under reduced pressure at 20° C. for 12 hours. Then, the copolymer was dissolved in an aqueous solution of sodium hydrogen carbonate adjusted to pH 8 to remove hydrochloric acid, and moisture was removed using an evaporator to give a vinylpyrrolidone/vinyl acetate/allylamine random copolymer.

From the measurement results of $^1$H-NMR, the mole fractions of vinylpyrrolidone, vinyl acetate, and allylamine to all the constituent monomer units were 58.0%, 40.0%, and 2.0%, respectively. In addition, the number average molecular weight of the copolymer calculated from the measurement result of GPC was 3,700. The copolymer was designated as Copolymer K. In Copolymer K, the number of carbon atoms at an end of a side chain of vinyl carboxylate is 1.

The number of carbon atoms, the mole fraction of each monomer unit, and the number average molecular weight of Examples 1 to 7 and Comparative Examples 1 to 4 are summarized in Table 1.

TABLE 1

| | Copolymer | | Number of carbon atoms of $R_B$ | Mole fraction of monomer unit A (%) | Mole fraction of monomer unit B (%) | Mole fraction of monomer unit C (%) | Number average molecular weight |
|---|---|---|---|---|---|---|---|
| Example 1 | Copolymer A | Vinylpyrrolidone/vinyl propanoate/allylamine random copolymer | 2 | 72.0 | 25.0 | 3.0 | 4,300 |
| Example 2 | Copolymer B | Vinylpyrrolidone/vinyl propanoate/allylamine random copolymer | 2 | 58.8 | 40.0 | 1.2 | 11,000 |
| Example 3 | Copolymer C | Vinylpyrrolidone/vinyl propanoate/allylamine random copolymer | 2 | 48.0 | 20.0 | 32.0 | 2,700 |
| Example 4 | Copolymer D | Vinylacetamide/vinyl pivalate/allylamine random copolymer | 4 | 48.0 | 50.0 | 2.0 | 4,600 |
| Example 5 | Copolymer E | Vinylpyrrolidone/vinyl myristate/allylamine random copolymer | 13 | 78.0 | 20.0 | 2.0 | 3,800 |
| Example 6 | Copolymer F | Vinylpyrrolidone/vinyl propanoate/2-isocyanatoethyl acrylate random copolymer | 2 | 75.0 | 23.0 | 2.0 | 3,500 |

TABLE 1-continued

| | Copolymer | | Number of carbon atoms of $R_B$ | Mole fraction of monomer unit A (%) | Mole fraction of monomer unit B (%) | Mole fraction of monomer unit C (%) | Number average molecular weight |
|---|---|---|---|---|---|---|---|
| Example 7 | Copolymer G | Vinylpyrrolidone/vinyl propanoate/glycidyl methacrylate random copolymer | 2 | 71.0 | 26.0 | 3.0 | 15,200 |
| Comparative Example 1 | Copolymer H | Vinylpyrrolidone/vinyl propanoate random copolymer | 2 | 60.0 | 40.0 | 0.0 | 12,500 |
| Comparative Example 2 | Copolymer I | Vinylpyrrolidone/vinyl propanoate/ allylamine random copolymer | 2 | 37.0 | 18.0 | 45.0 | 1,200 |
| Comparative Example 3 | Copolymer J | Vinylpyrrolidone/vinyl propanoate/ allylamine random copolymer | 2 | 56.0 | 43.6 | 0.4 | 10,600 |
| Comparative Example 4 | Copolymer K | Vinylpyrrolidone/vinyl acetate/ allylamine random copolymer | 1 | 58.0 | 40.0 | 2.0 | 3,700 |

Example 8

A plate material of SUS304 (length: 1 cm×width: 0.5 cm, hereinafter referred to as "SUS plate") was used as a metal. As a metal cleaning step, the plate material was subjected to ultrasonic cleaning and cleaning with a piranha solution. First, the SUS plate was subjected to ultrasonic cleaning in the order of hexane, acetone, methanol, and distilled water (twice), and dried under vacuum. Then, the SUS plate was immersed in a piranha solution for 1 hour, ultrasonically cleaned 5 times with distilled water, and then dried under vacuum. Using 10-carboxydecylphosphonic acid (hereinafter referred to as "10-CDPA") that is a compound represented by the general formula (VI), the SUS plate was subjected to ultrasonic treatment in xylene to give a suspension containing 1 mM of 10-CDPA. As an immersion step, the SUS plate after the metal cleaning step was immersed in the xylene suspension containing 10-CDPA at 37° C. for 6 hours and taken out. After being dried under vacuum, the SUS plate was heated at 130° C. for 48 hours to chemically bond the metal with 10-CDPA. The SUS plate was ultrasonically cleaned with tetrahydrofuran and methanol to remove 10-CDPA not chemically bonded to the metal, and then dried under vacuum.

Then, the SUS plate was immersed in an aqueous solution of 0.5 wt % DMT-MM (manufactured by Wako Pure Chemical Industries, Ltd.) and 5.0 wt % Copolymer A, and reacted at 50° C. for 2 hours to covalently bond Copolymer A to the carboxy group of 10-CDPA. The aqueous solution after the reaction was removed, and the SUS plate was cleaned with distilled water. As a result of the blood coagulation test, thrombosis was not observed, and the percentage of the area where thrombi adhered was 0%.

Comparative Example 5

An untreated SUS plate was prepared, and a blood coagulation test was carried out. Thrombi were formed on the whole surface of the SUS plate, and the percentage of the area where thrombi adhered was 100%.

Example 9

As a base material, a polypropylene plate material (length: 1 cm×width: 1 cm, hereinafter referred to as "PP plate") was used. A surface of the PP plate was subjected to plasma treatment to form a carboxy group. The PP plate was immersed in an aqueous solution of 0.5 wt % DMT-MM and 5.0 wt % Copolymer A, and reacted at 50° C. for 2 hours to covalently bond Copolymer A to the carboxy group on the surface of the PP plate. The aqueous solution after the reaction was removed, and the PP plate was cleaned with distilled water. As a result of the blood coagulation test, thrombosis was not observed, and the percentage of the area where thrombi adhered was 0%.

Comparative Example 6

An untreated PP plate was prepared, and a blood coagulation test carried out. Thrombi were formed on the whole surface of the PP plate, and the percentage of the area where thrombi adhered was 100%.

Example 10

A PET mesh (length: 1 cm×width: 1 cm, single yarn diameter: 27 μm, opening: 100 μm) as a base material was immersed in an aqueous solution of 3.0 wt % potassium permanganate (manufactured by Wako Pure Chemical Industries, Ltd.) and 0.6 mol/L sulfuric acid (manufactured by Wako Pure Chemical Industries, Ltd.), and reacted at 60° C. for 3 hours to hydrolyze and oxidize the PET mesh. The aqueous solution after the reaction was removed, and the PET mesh cleaned with 6 N hydrochloric acid (manufactured by Wako Pure Chemical Industries, Ltd.) and distilled water.

Then, the PET mesh was immersed in an aqueous solution of 0.5 wt % DMT-MM and 5.0 wt % Copolymer A, and reacted at 50° C. for 2 hours to covalently bond Copolymer A to the PET mesh. The aqueous solution after the reaction was removed, and the PET mesh cleaned with distilled water. As a result of XPS measurement, the abundance rate of nitrogen atoms was 4.6 at %. In addition, as a result of the blood coagulation test, thrombosis was not observed, and the percentage of the area where thrombi adhered was 0%.

Example 11

A PET mesh was treated in the same manner as in Example 10 except that Copolymer B was used instead of Copolymer A. As a result of XPS measurement, the abundance rate of nitrogen atoms was 1.8 at %. In addition, as a result of the blood coagulation test, thrombosis was hardly observed, and the percentage of the area where thrombi adhered was 5%.

Example 12

After the steps of Example 9, the PET mesh was immersed in an aqueous solution of 0.5 wt % DMT-MM (manufactured by Wako Pure Chemical Industries, Ltd.) and 5.0 wt % Copolymer B, and reacted at 50° C. for 2 hours to covalently bond Copolymer B to the PET mesh. The aqueous solution after the reaction was removed, and the PET mesh cleaned with distilled water. As a result of XPS measurement, the abundance rate of nitrogen atoms was 4.0 at %. In addition, as a result of the blood coagulation test, thrombosis was not observed, and the percentage of the area where thrombi adhered was 0%.

Example 13

A PET mesh was treated in the same manner as in Example 10 except that Copolymer C was used instead of Copolymer A. As a result of the blood coagulation test, thrombosis was hardly observed, and the percentage of the area where thrombi adhered was 10%.

Example 14

A PET mesh was treated in the same manner as in Example 10 except that Copolymer D was used instead of Copolymer A. As a result of the blood coagulation test, thrombosis was not observed, and the percentage of the area where thrombi adhered was 0%.

Example 15

A PET mesh was treated in the same manner as in Example 10 except that Copolymer E was used instead of Copolymer A. As a result of the blood coagulation test, the percentage of the area where thrombi adhered was 15%.

Comparative Example 7

An untreated PET mesh was prepared, and a blood coagulation test was carried out. As a result, thrombi were formed on the whole surface, and the percentage of the area where thrombi adhered was 100%.

Comparative Example 8

A 10 ppm aqueous solution of a vinylpyrrolidone/vinyl acetate copolymer (Kollidon VA64 (registered trademark) manufactured by BASF) was adjusted, and an untreated PET mesh immersed in the aqueous solution. The PET mesh was irradiated with 25 kGy of γ-rays to cross-link and immobilize the vinylpyrrolidone/vinyl acetate copolymer. The PET mesh was cleaned with distilled water, and a blood coagulation test carried out. As a result, thrombi were formed on the whole surface, and the percentage of the area where thrombi adhered was 100%. This is probably because the number of carbon atoms at an end of a side chain of the monomer unit B in the vinylpyrrolidone/vinyl acetate copolymer was 1, and the vinylpyrrolidone/vinyl acetate copolymer was crosslinked and immobilized and was insufficient in antithrombotic properties.

Comparative Example 9

A PET mesh was crosslinked and immobilized in the same manner as in Comparative Example 8 except that Copolymer H was used instead of the vinylpyrrolidone/vinyl acetate copolymer. As a result of the blood coagulation test, the percentage of the area where thrombi adhered was 95%. This is probably because Copolymer H was crosslinked and immobilized and did not exhibit sufficient antithrombotic properties.

Comparative Example 10

A PET mesh was treated in the same manner as in Example 10 except that polyethyleneimine (LUPASOL (registered trademark) manufactured by BASF) was used instead of Copolymer A. As a result of the blood coagulation test, thrombi were formed on the whole surface, and the percentage of the area where thrombi adhered was 100%. This is probably because polyethyleneimine did not have the monomer units A and B and was not excellent in antithrombotic properties.

Comparative Example 11

A PET mesh was treated in the same manner as in Example 10 except that Copolymer H was used instead of Copolymer A. As a result of the blood coagulation test, thrombi were formed on the whole surface, and the percentage of the area where thrombi adhered was 100%. This is probably because Copolymer E did not have a reactive functional group in the monomer unit C and was not immobilized on the surface.

Comparative Example 12

A PET mesh was treated in the same manner as in Example 10 except that Copolymer I was used instead of Copolymer A. As a result of the blood coagulation test, the percentage of the area where thrombi adhered was 95%. This is probably because the mole fraction of allylamine based on all the monomer units that constitute Copolymer I was large, and Copolymer I was insufficient in antithrombotic properties.

Comparative Example 13

A PET mesh was treated in the same manner as in Example 10 except that Copolymer J was used instead of Copolymer A. As a result of the blood coagulation test, thrombi were formed on the whole surface, and the percentage of the area where thrombi adhered was 100%. This is probably because the mole fraction of allylamine based on all the monomer units that constitute Copolymer J was small, and only small amount of Copolymer J was immobilized onto the surface.

Comparative Example 14

A PET mesh was treated in the same manner as in Example 10 except that Copolymer K was used instead of Copolymer A. As a result of the blood coagulation test, the percentage of the area where thrombi adhered was 80%. This is probably because the number of carbon atoms at an end of a side chain of the monomer unit B in Copolymer I was 1, and Copolymer I was insufficient in antithrombotic properties.

Example 16

The PET mesh produced in Example 10 was cut into a circle having a diameter of 1.0 cm. This was used as a filter to produce a thrombus capture device, and a blood circulation test was carried out. Thrombosis was not observed on the surface of the filter formed of the PET mesh to which Copolymer A was covalently bonded, and the percentage of the area where thrombi adhered was 0%.

Comparative Example 15

An untreated PET mesh was cut into a circle having a diameter of 1.0 cm. This was used as a filter to produce a thrombus capture device, and a blood circulation test was carried out. Thrombi were formed on the whole surface of the filter formed of the PET mesh, and the percentage of the area where thrombi adhered was 100%.

Example 17

As a base material, a polyvinyl chloride plate material (length: 1 cm×width: 1 cm, hereinafter referred to as "vinyl chloride plate") was used. The vinyl chloride plate was immersed in a tetrahydrofuran solution of a 1.0 wt % vinyl chloride/vinyl alcohol random copolymer (VINNOL E15/48A (registered trademark) manufactured by TOMOE ENGINEERING CO., LTD.) for 3 minutes and coated therewith to introduce a hydroxyl group onto the surface. Then, the vinyl chloride plate was immersed in a tetrahydrofuran solution of 5.0 wt % Copolymer F for 3 minutes, dried under vacuum, and reacted at 50° C. for 2 hours for covalent bonding. As a result of the blood coagulation test, the percentage of the area where thrombi adhered was 10%.

Example 18

A tetrahydrofuran solution of 5 wt % Copolymer F and a 1.5 wt % vinyl chloride/vinyl alcohol random copolymer (VINNOL E15/48A (registered trademark) manufactured by TOMOE ENGINEERING CO., LTD.) was prepared and reacted at 70° C. for 2 hours, and the reaction product poured into pure water. The deposited white precipitate was collected and dried under reduced pressure at 20° C. for 12 hours to give a graft copolymer composed of the vinyl chloride/vinyl alcohol random copolymer and Copolymer F. The vinyl chloride plate was immersed in a tetrahydrofuran solution of the 5.0 wt % graft copolymer for 3 minutes to introduce Copolymer F in the form of the graft copolymer onto the surface of the base material. As a result of the blood coagulation test, thrombosis was not observed, and the percentage of the area where thrombi adhered was 0%.

Example 19

A tetrahydrofuran solution of 5 wt % Copolymer G and a 1.5 wt % vinyl chloride/vinyl alcohol random copolymer (VINNOL E15/48A (registered trademark) manufactured by TOMOE ENGINEERING CO., LTD.) was prepared and reacted at 80° C. for 5 hours, and the reaction product poured into pure water. The deposited white precipitate was collected and dried under reduced pressure at 20° C. for 12 hours to give a graft copolymer composed of the vinyl chloride/vinyl alcohol random copolymer and Copolymer G. The vinyl chloride plate was immersed in a tetrahydrofuran solution of the 5.0 wt % graft copolymer for 3 minutes to introduce Copolymer G in the form of the graft copolymer onto the surface of the base material. As a result of the blood coagulation test, the percentage of the area where thrombi adhered was 5%.

Comparative Example 16

An untreated vinyl chloride plate was prepared, and a blood coagulation test was carried out. As a result, thrombi were formed on the whole surface, and the percentage of the area where thrombi adhered was 100%.

The blood coagulation test of Examples 8 to 15 and 17 to 19, and Comparative Examples 5 to 14 and 16 is summarized in Table 2. The blood circulation test of Example 16 and Comparative Example 15 is summarized in Table 3.

TABLE 2

| | Immobilized material | Base material | Area where thrombi adhered (%) |
|---|---|---|---|
| Example 8 | Copolymer A | SUS plate | 0 |
| Comparative Example 5 | — | SUS plate | 100 |
| Example 9 | Copolymer A | PP plate | 0 |
| Comparative Example 6 | — | PP plate | 100 |
| Example 10 | Copolymer A | PET mesh | 0 |
| Example 11 | Copolymer B | PET mesh | 5 |
| Example 12 | Copolymer A, Copolymer B | PET mesh | 0 |
| Example 13 | Copolymer C | PET mesh | 10 |
| Example 14 | Copolymer D | PET mesh | 0 |
| Example 15 | Copolymer E | PET mesh | 15 |
| Comparative Example 7 | — | PET mesh | 100 |
| Comparative Example 8 | Vinylpyrrolidone/vinyl acetate copolymer | PET mesh | 100 |
| Comparative Example 9 | Copolymer H | PET mesh | 95 |
| Comparative Example 10 | Polyethyleneimine | PET mesh | 100 |
| Comparative Example 11 | Copolymer H | PET mesh | 100 |
| Comparative Example 12 | Copolymer I | PET mesh | 95 |
| Comparative Example 13 | Copolymer J | PET mesh | 100 |
| Comparative Example 14 | Copolymer K | PET mesh | 80 |
| Example 17 | Copolymer F | Vinyl chloride plate | 10 |
| Example 18 | Copolymer F | Vinyl chloride plate | 0 |
| Example 19 | Copolymer G | Vinyl chloride plate | 5 |
| Comparative Example 16 | — | Vinyl chloride plate | 100 |

TABLE 3

| | Immobilized material | Base material | Area where thrombi adhered (%) |
|---|---|---|---|
| Example 16 | Copolymer A | PET mesh | 0 |
| Comparative Example 15 | — | PET mesh | 100 |

INDUSTRIAL APPLICABILITY

Since our copolymer has potent antithrombotic properties and can be immobilized onto the surface of a medical material, it can be used in a wide range of medical materials and medical devices.

The invention claimed is:
1. A medical material containing the comprising:
   a copolymer comprising a monomer unit A, a monomer unit B, and a monomer unit C represented by general formula (I),
   wherein a mole fraction of the monomer unit C based on all monomer units that constitute the copolymer is 0.5 to 40%:

A

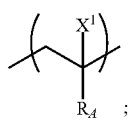

B

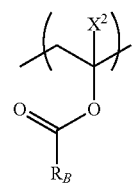

C

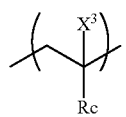

wherein $R_A$ represents a functional group having an amide bond; $R_B$ represents an alkyl or an alkenyl having 2 to 20 carbon atoms; $R_C$ represents an alkyl or an alkenyl in which 1) an arbitrary hydrogen atom is substituted with at least one functional group selected from the group consisting of an amino group, an azido group, an imino group, a carboxy group, an acid chloride group, an acid anhydride group, an aldehyde group, a hydroxyl group, a phosphoric acid group, a thiol group, an isocyanate group, a thioisocyanate group, an epoxy group, a halogenated alkyl group, a cyano group, a vinyl group, an ethynyl group, a nitro group and a nitroso group, and ionized functional groups thereof, and 2) an arbitrary carbon atom in the alkyl or the alkenyl of $R_C$ is optionally substituted with a nitrogen atom, an oxygen atom, or a sulfur atom; and $X^1$, $X^2$, and $X^3$ each represent a hydrogen atom or a methyl group, and a base material bonded to the copolymer.

2. The medical material according to claim 1, wherein the base material is made from a polymer having a repeating unit containing an ester bond in a main chain.

3. The medical material according to claim 1, wherein the copolymer has a number average molecular weight of 1,000 to 100,000.

4. The medical material according to claim 1, wherein the copolymer Rc is an alkyl group in which an arbitrary hydrogen atom is substituted with at least one functional group selected from the group consisting of an amino group, an isocyanate group, and an epoxy group.

5. The medical material according to claim 1, wherein a ratio of an N1s peak area to a total peak area is 1.0 to 20.0 at % on a surface of the base material by an XPS measurement.

6. A thrombus capture device including the medical material according to claim 1.

7. The medical material according to claim 1, wherein the base material is made from a polymer a part of which contains a hydroxyl group or a carboxy group introduced therein and in which at least one hydrogen atom in a main chain is substituted with a chlorine atom, or a polymer a part of which contains a hydroxyl group or a carboxy group introduced therein and that has a siloxane bond in at least a part thereof, and the copolymer is bonded to the base material via the hydroxyl group or the carboxy group.

8. A blood circuit including the medical material according to claim 7.

9. A medical material comprising a copolymer, a base material, and a phosphonic acid derivative or a catechol derivative,
wherein the copolymer comprises a monomer unit A, a monomer unit B, and a monomer unit C represented by general formula (I),
a mole fraction of the monomer unit C based on all monomer units that constitute the copolymer is 0.5 to 40%:

A

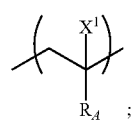

B

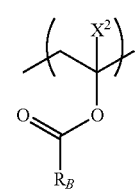

C

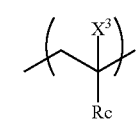

wherein $R_A$ represents a functional group having an amide bond, $R_B$ represents an alkyl or an alkenyl having 2 to 20 carbon atoms, Rc represents an alkyl or an alkenyl in which an arbitrary hydrogen atom is substituted with at least one functional group selected from the group consisting of an amino group, an azido group, an imino group, a carboxy group, an acid chloride group, an acid anhydride group, an aldehyde group, a hydroxyl group, a phosphoric acid group, a thiol group, an isocyanate group, a thioisocyanate group, an epoxy group, a halogenated alkyl group, a cyano group, a vinyl group, an ethynyl group, a nitro group and a nitroso group, and ionized functional groups thereof (wherein an arbitrary carbon atom in the alkyl or the alkenyl of Rc is optionally substituted with a nitrogen atom, an oxygen atom, or a sulfur atom), and $X^1$, $X^2$, and $X^3$ each represent a hydrogen atom or a methyl group,
the base material is made of a metal,
the copolymer is bonded to the phosphonic acid derivative or the catechol derivative,
the phosphonic acid derivative is bonded to the base material via a phosphonic acid group thereof, and
the catechol derivative is bonded to the base material via a catechol group thereof.

10. The medical material according to claim 9, wherein the copolymer has a number average molecular weight of 1,000 to 100,000.

11. The medical material according to claim 9, wherein the copolymer Rc is an alkyl group in which an arbitrary hydrogen atom is substituted with at least one functional group selected from an amino group, an isocyanate group, and an epoxy group.

12. The medical material according to claim 9, wherein a ratio of an N1s peak area to a total peak area is 1.0 to 20.0 at % on a surface of the base material by an XPS measurement.

* * * * *